United States Patent [19]
Mulder et al.

[11] Patent Number: 5,256,380
[45] Date of Patent: Oct. 26, 1993

[54] STARTUP OPENINGS IN A THREE-PHASE GASLIFT LOOP REACTOR

[75] Inventors: Arnold Mulder, Delft; Rene Weltevrede, Rotterdam, both of Netherlands

[73] Assignee: Paques B.V., Balk, Netherlands

[21] Appl. No.: 689,453

[22] Filed: Apr. 22, 1991

Related U.S. Application Data

[63] Continuation of Ser. No. 297,073, Jan. 13, 1989, abandoned.

[30] Foreign Application Priority Data

Jan. 20, 1988 [EP] European Pat. Off. ........ 08-200104.3

[51] Int. Cl.$^5$ .............................................. B01F 5/00
[52] U.S. Cl. .................................. 422/231; 422/139; 422/140; 435/288; 435/314
[58] Field of Search ............... 422/310, 139, 140, 312, 422/231; 435/288, 314

[56] References Cited

U.S. PATENT DOCUMENTS 3,236,744  2/1966  Yamaha .............................. 435/314
3,957,585  5/1976  Malick ................................ 435/246

OTHER PUBLICATIONS

*Hysteresis Effects in Suspended Solid Particles in Bubble Columns With and Without Draft Tube*, Heck, J. and Onken, U., Chemical Engineering Science, vol. 42, No. 5, pp. 1211–1212.

Primary Examiner—Robert J. Warden
Assistant Examiner—Christopher Y. Kim
Attorney, Agent, or Firm—Bierman & Muserlian

[57] ABSTRACT

Reduction of the hysteresis effects in a gaslift loop reactor is effected with a draft tube for solids suspension. The gas or liquid flow rates for generating complete solid suspension are significantly higher than the flow rates necessary for maintaining that state. These hysteresis effects may be significantly reduced and a substantial reduction is obtained for the energy necessary to obtain the state of suspension. Preferably a draft tube which comprises openings through which an extra circulation takes place especially during the startup phase is used.

3 Claims, 1 Drawing Sheet

STARTUP OPENINGS IN A THREE-PHASE GASLIFT LOOP REACTOR

This is a continuation of Ser. No. 297,073 filed Jan. 13, 1989, abandoned.

The present invention relates to a draft tube for use in a three-phase gaslift loop reactor and to a process in which such a draft tube is used.

Gaslift loop reactors with suspended solid particles are applied in many chemical and biotechnological processes. Examples of such processes are catalytic methanation, the conversion of synthesis gas into e.g. hydrocarbons, $SO_2$ oxidation, catalytic hydrogenation, microbial desulfurization of coal, biological waste water treatment and processes for the production of compounds using immobilized micro-organisms such as bacteria, yeasts, fungi. The latter processes can be exemplified by (a) the anaerobic production of alcohols such as ethanol, butanol, isopropyl alcohol, using an inert gas such as nitrogen during starting up and later on gases formed during the reaction may be used or (b) aerobic production of compounds such as penicillin, enzymes.

During the startup of bubble columns and gaslift reactors with suspended solids severe problems may occur in obtaining a state of suspension of solid particles. It appears that in order to obtain a state of suspension of solid particles in a three-phase gaslift reactor a much higher gas velocity is necessary compared to the gas velocity which is thereafter used to maintain this state of suspension. This problem is explained in detail by J. Heck and U. Onken (Chem. Ing. Techn. 58 (1986) no. 2, p. 131–133 and Chemical Engineering Science 42 (1987) no. 5, p. 1211–1212). In these articles hysteresis effects are demonstrated, which occur between generating and maintaining complete solids suspension.

FIG. 1, which is freely borrowed from these articles, shows the results of a pressure drop ($\Delta p$) measurement in a system of air/water/glass particles without draft tube as a function of the superficial gas velocity (Vsg). The state of suspension was determined by measuring the pressure drop over a bubble column. With increasing gas velocity (A→B in FIG. 1) the pressure drop increases with the amount of solid particles in suspension. At a definite gas flow rate a steplike rise of pressure (B→C) occurs. At this point the state of complete solids suspension is reached. Further increase (C→D) does not result in any substantial further rise of pressure drop. When the gas velocity is decreased (D→E), the state of complete solid suspension is maintained. Only at point E does the pressure drop undergo a steplike decrease. The authors of the above articles clearly demonstrate that the gas flow rates required for generating complete solids suspension are significantly higher than the gas flow rates for maintaining that state.

In the articles the hysteresis effect was also examined in suspended solids bubble columns with a draft tube. A comparison of the results showed that the minimum gas velocity for maintaining the state of complete solid suspension is much smaller in a bubble column with draft tube, than in a simple bubble column. Moreover the gas flow rate for generating the state of complete solid suspension in a bubble column with draft tube is evidently higher than that in the bubble column without draft tube. The hysteresis effects in a bubble column with a draft tube will therefore be even more significant than these effects in a simple column as shown in FIG. 1.

In practice it is found that in a gaslift loop reactor with a draft tube in which there is no gasflow that the solids are settling at the bottom of the reactor. These solids act as a plug in the gaslift reactor when the gasflow is started. The solids which are not part of this plug are suspended in the reactor. In this startup period hardly any solids can be found in the space above the plug of solids. The startup does not occur properly, because the solids brought into suspension from one side of the plug of solids, settle on the other part of the plug. For example, using a gaslift reactor with a draft tube, wherein an upward flow exists, part of the solids at the top of the plug in the draft tube are brought into suspension, but these solids settle easily outside the draft tube. The solids in the plug move only slighty, thereby maintaining the contours of the plug.

The problem of the necessity of a very high gas velocity for bringing the solid particles into complete suspension, which is much higher than the gas velocity necessary thereafter to maintain this state of suspension, does not play an important role on small lab scale experiments. By increasing the gas velocity, a state of suspension is easily obtained. Sofar only the increase of the gas velocity to generate the state of suspension has been mentioned, but a sufficient increase of the liquid velocity results in this state as well. In fact a certain amount of energy has to be dispersed in the system before this system attains the state of solid suspension. This initial energy is higher than the energy which has to be added to keep the system in a state of suspension.

On a larger lab scale or pilot plant scale, the equipment has to be adapted in order to make such high gas and/or liquid velocities possible, while on commercial full scale reactors it is uneconomical, because not only do the inlets for the liquid and gas have to be overdimensioned but also the dimensions of pumps and compressors have to be excessive, or the quantities of gas or liquid necessary to overcome the hysteresis effects have to be extravagant.

It is the object of the invention to reduce significantly the hysteresis effects in a gaslift reactor with a draft tube. The reduction of the hysteresis is based on a substantial reduction of the energy necessary to obtain the state of suspension. This may give rise to, for example, a lower gas and/or liquid velocity necessary in the startup period of this gaslift reactor in comparison with that of a conventional gaslift reactor. According to one aspect of the invention a draft tube for use in a gaslift reactor comprises a tube with one or more startup openings.

In many processes air will be used as gas.

Figure 1:
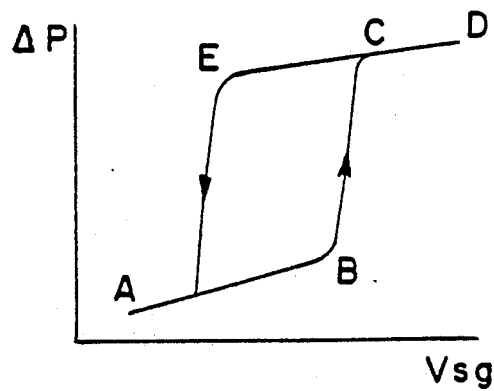
FIG. 1 shows the hysteresis effects in a gaslift reactor.
Figure 2:
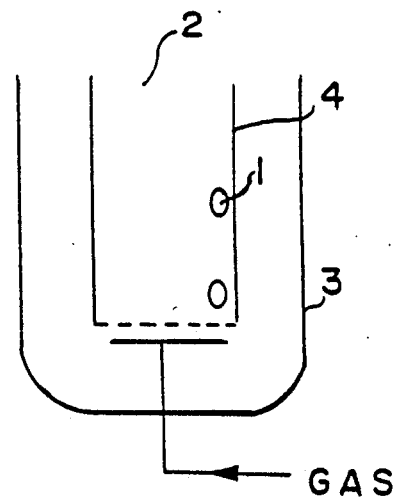
FIG. 2 shows circular openings in the draft tube.

In an embodiment of the invention one or more startup openings (1) are present in the draft tube (4) for use in a gaslift reactor (3) (see FIG. 2). The startup openings according to the invention are specially made and do not comprise the normal inlets and outlets (2) of a tube. The total area of these openings is preferably 0.001 to 20% of area A or area B, whichever is the smaller. Area A is the cross sectional area of the draft tube and area B is the cross sectional area of the reactor minus the cross sectional area of the draft tube. More preferably the total area of these openings is 0.1 to 10% of area A or area B, whichever is the smaller, advantageously 0.5 to 7%.

Figure 3:
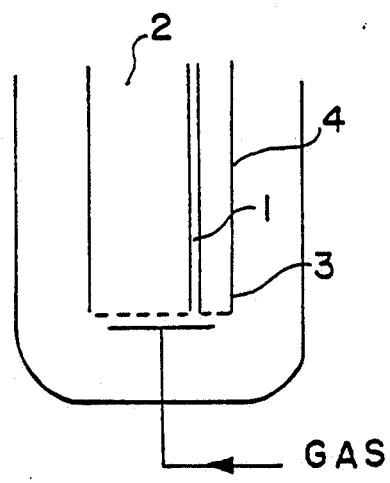
FIG. 3 shows an elongate opening in the axial direction.
Figure 4:
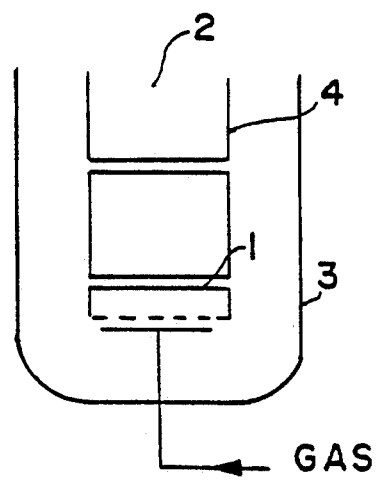
FIG. 4 shows an elongate opening situated perpendicular to the axial direction.

The startup openings may have any form. In practice for example circular openings (FIG. 2) or elongate openings can be used. Elongate openings in the draft tube may extend in the axial direction of the draft tube (FIG. 3), or may extend oblique to this axial direction, or preferably may extend perpendicular to the axial direction of the draft tube (FIG. 4). When an elongate opening is used which extends in the axial direction of the draft tube, measures sometimes have to be taken to prevent the shutting of this opening during operational conditions. When starting from the situation with settled solids, an opening in the draft tube with a substantial area is necessary during the start-up of the gaslift loop process in order to obtain an initial circulation. Using a slit in the axial direction of the draft tube the opening area is determined by the width of the slit. If the slit is as long as the draft tube, the total opening area can be too large during stationary conditions resulting in a shortcircuiting or may result in only a partial start-up of the process.

As will be appreciated by a person skilled in the art, two or more draft tubes in the reactor are of course possible as well. In such case at least one of the draft tubes may be equipped with the startup openings (1) as described hereinbefore. The draft tube will generally have a cylindrical form. Other forms of the draft tube, such as a truncated cone or two or more tubes of different diameter united together are comprised by the present invention as well.

Preferably at least part of the total area of the opening(s) is situated above the level of the settled solids or is situated only very little below this level.

The total area of the opening(s) and the level of the terminations of the openings will be determined e.g. by the ratio of height and cross sectional area of the sunken solids and by the bulk density of the solids.

The proper dimension of the startup openings can easily be determined by the person skilled in the art.

The advantageous effect of the startup opening(s) in the draft tube may be explained by the presence of a circulation through the opening(s) in the upper part around the draft tube which gives more solids the opportunity to become suspended. This extra circulation takes place especially during the startup phase in order to stimulate the suspension of the solids. If this additional circulation stream becomes sufficient, superficial velocities may arise in the riser and downcomer, which are above the terminal settling velocity of the particles. The quantity of solid particles whirled up by the gas or liquid supply, will be maintained in suspended condition. The total possible amount of solids thus being suspended depends mainly on the gas or liquid supply, the area of the opening, the magnitude of the circulation through this opening. After the startup the plug of solids at the bottom of the reactor disappears, the circulation will then become possible underneath the underside of the draft tube and the above described circulation is accelerated. The three-phase gaslift reactor has now physically started up.

The above explanation is offered merely to show the unexpected nature of the solution of the problem underlying the invention and is intended neither to define nor to limit the invention in any manner.

The invention includes the use of the draft tube as a riser or as a downcomer in a three-phase gaslift reactor.

The following experimental data are given to illustrate the invention, however without restricting the scope of the invention.

EXAMPLE 1

To a 2 litre glass reactor having a diameter of 5 cm, 400 g of sand was added and the reactor was filled with water. In the reactor a draft tube of 3 cm in diameter and 74 cm of length was situated in the middle of the reactor 1.2 cm above the bottom of the reactor (see FIG. 2).

Air was supplied in the center of the bottom of the reactor. No liquid was supplied.

A. Draft tube without startup openings.

| gas supply (l/h) | Vsg (cm/s) | results |
|---|---|---|
| 480 | 7 | after 15 h still no circulation |
| 800 | 12 | after 10 min. still no circulation |

Vsg = superficial gas velocity in the reactor calculated on the total cross sectional area of the reactor.

B. Draft tube with 3 startup openings each with a diameter of 0.6 cm situated at 3, 6 and 9 cm above the bottom of the draft tube.

| gas supply (l/h) | Vsg (cm/s) | results |
|---|---|---|
| 320 | 5 | after 72 minutes no complete circulation, only circulation around the upper part of the tube down to the lowest situated opening |
| 480 | 7 | after 2 minutes state of complete suspension |

C. Draft tube with 5 startup openings each with a diameter of 0.6 cm situated as follows: two at 3 cm from the bottom and three at 6.5 cm from the bottom of the draft tube.

| gas supply (l/h) | Vsg (cm/s) | results |
|---|---|---|
| 240 | 4 | after 13 minutes state of complete suspension |
| 480 | 7 | after 1 minute state of complete suspension |

As shown above the distance to the bottom of the draft tube and the total area of the openings determine the reduction of the gas flow necessary to obtain the state of complete suspension.

EXAMPLE 2

To a 25 litre glass reactor having a diameter of 10 cm, 2.5 kg of sand was added and the reactor was filled with water. In the reactor a draft tube 7.4 cm in diameter and 200 cm long was situated in the middle of the reactor 2 cm above the bottom of the reactor (see FIG. 2).

Air was supplied in the center and at the bottom of the reactor. No liquid was supplied.

A. Draft tube without startup openings.

| gas supply (1/h) | Vsg (cm/s) | results |
|---|---|---|
| 1300 | 5 | no state of complete suspension |
| 1670 | 6 | no state of complete suspension |
| 2000 | 8 | no state of complete suspension |
| 2340 | 9 | only partly a state of suspension |

B. Draft tube with nine startup openings each with a diameter of 1 cm situated as follows: three sets of three openings at distances of 15 cm, 30 cm and 45 cm respectively from the bottom of the draft tube.

In this experiment the amount of sand added to the reactor was varied.

| gas supply (1/h) | Vsg (cm/s) | sand added (kg) | results |
|---|---|---|---|
| 1300 | 5 | 1.25 | state of complete suspension |
| 1300 | 5 | 2.50 | state of complete suspension |
| 1300 | 5 | 3.75 | state of complete suspension |
| 1300 | 5 | 5.00 | state of complete suspension |
| 1300 | 5 | 6.25 | only partly a state of suspension |

This experiment shows the effect of the openings in the draft tube on the reduction of the gas flow necessary to obtain the state of complete suspension.

I claim:

1. In a process for reducing the hysteresis effects in a gaslift loop reactor consisting essentially of a reaction vessel filled with at least 50 grams of suspended solid particles comprising immobilized microorganisms per liter of reaction vessel volume which are settled at the bottom of the reaction vessel before the startup of the gaslift loop process, wherein the improvement comprises providing a draft tube having at least one start up opening for establishing an additional circulation steam during the startup phase in order to stimulate the suspension of solids and means for introducing a gas at the bottom of said reaction vessel for creating a suspension of solid particles at the bottom of a gaslift loop through the draft tube to reduce the energy necessary to obtain suspension.

2. A gaslift loop reactor of claim 1 wherein each of said at least one opening have a substantially circular form.

3. The process of claim 1 wherein the gas is air.

* * * * *